(12) United States Patent
Rekhter et al.

(10) Patent No.: US 10,138,244 B2
(45) Date of Patent: Nov. 27, 2018

(54) TRIAZOLOPYRAZINONE DERIVATIVE USEFUL AS A HUMAN PDE1 INHIBITOR

(71) Applicant: Eli Lilly and Company, Indianapolis, IN (US)

(72) Inventors: Mark David Rekhter, Carmel, IN (US); Qing Shi, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/680,250

(22) Filed: Aug. 18, 2017

(65) Prior Publication Data

US 2018/0057494 A1    Mar. 1, 2018

Related U.S. Application Data

(60) Provisional application No. 62/379,372, filed on Aug. 25, 2016.

(51) Int. Cl.
*A61K 31/5025* (2006.01)
*C07D 471/14* (2006.01)

(52) U.S. Cl.
CPC .................. *C07D 471/14* (2013.01)

(58) Field of Classification Search
CPC ... A61K 31/25; A61K 31/5025; C07D 471/14
USPC .......................................... 514/250; 544/346
See application file for complete search history.

(56) References Cited

U.S. PATENT DOCUMENTS

| | | |
|---|---|---|
| 8,299,080 B2 | 10/2012 | Okada et al. |
| 9,175,010 B2 | 11/2015 | Branstetter et al. |
| 2010/0048556 A1 | 2/2010 | Okada et al. |

FOREIGN PATENT DOCUMENTS

| | | |
|---|---|---|
| EP | 0040401 A1 | 11/1981 |
| EP | 2103613 A1 | 9/2009 |
| EP | 2615096 A1 | 7/2013 |
| WO | 2008/103357 A1 | 8/2008 |
| WO | 2016/055618 A1 | 4/2016 |
| WO | 2017/139186 A1 | 8/2017 |

OTHER PUBLICATIONS

Al-Salahi, Rashad "Synthesis of Novel 2-Alkoxy(aralkoxy)-4H-[1,2,4]triazolo[1,5-a]quinazolin-5-ones Starting with Dialkyl-N-Cyanoimidocarbonates", Journal of Heterocyclic Chemistry, (2011) vol. 48, pp. 656.
U.S. Appl. No. 15/423,626 pending in the USPTO, filed Feb. 3, 2017; Eli Lilly and Company.
Asier Unciti-Broceta, "Regioselective One-Pot Synthesis of 9-Alkyl-6-chloropyrido [3,2-e][1,2,4]Triazolo-[4,3-a]Pyrazines," The Journal of Organic chemistry, vol. 70(7), pp. 2878-2880, 2005.

*Primary Examiner* — Brenda L Coleman
(74) *Attorney, Agent, or Firm* — Nelsen L Lentz

(57) ABSTRACT

The present invention provides a compound of Formula I:

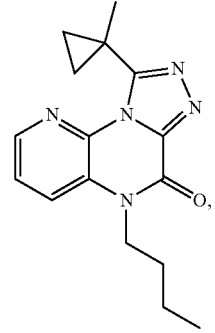

Formula I or a pharmaceutically acceptable salt thereof, for use as a human PDE1 inhibitor.

10 Claims, No Drawings

TRIAZOLOPYRAZINONE DERIVATIVE USEFUL AS A HUMAN PDE1 INHIBITOR

The present invention relates to a certain human PDE1 inhibitor, to pharmaceutical compositions comprising the compound, to methods of using the compound to treat physiological disorders, and to intermediates and processes useful in the synthesis of the compound.

Phosphodiesterases (PDEs) are enzymes that regulate the cellular levels of cAMP and cGMP by controlling the rate at which these cyclic nucleotides are hydrolyzed. PDE1, a calcium and calmodulin-dependent PDE, is one of at least 11 known PDE families PDE1 is expressed in many tissues, including the brain, heart, lung, kidney, and smooth muscle. In addition, PDE1 is comprised of a family of three known isoforms, PDE1A, PDE1B, and PDE1C.

Patients suffering from diabetes often develop a form of chronic kidney disease referred to as diabetic kidney disease (or diabetic nephropathy). It has been estimated that diabetic kidney disease may affect as many as 40 percent of diabetic patients. Treatment options for diabetic kidney disease is limited and includes use of medications that lower blood pressure, management of blood glucose levels, diet, and weight, and implementation of regular physical activity. Thus, there is a need for additional treatment choices for patients suffering from chronic kidney disease, particularly diabetic kidney disease.

U.S. Pat. No. 8,299,080 discloses certain quinoxaline derivatives having PDE9 inhibiting activity useful for treating various disorders such as dysuria and hypertension. In addition, European Patent No. 0 040 401 discloses certain substituted triazoloquinoxalin-4-ones possessing anti-hypertensive activity.

The present invention provides a certain novel compound that is an inhibitor of human PDE1. In addition, the present invention provides a certain novel compound that is a selective inhibitor of human PDE1A, PDE1B, and PDE1C relative to other human PDEs, such as PDE2A, PDE3A, PDE4D, PDE5A, PDE6AB, PDE7B, PDE8A, PDE9A, PDE10A, and PDE11A. Furthermore, the present invention provides a certain novel compound that may have antihypertensive effects and may also improve renal blood flow. In addition, the compound of the present invention may reduce renal fibrosis.

Accordingly, the present invention provides a compound of Formula I:

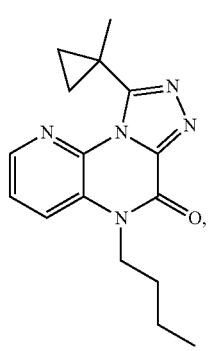

Formula I or a pharmaceutically acceptable salt thereof.

The present invention also provides a method of treating chronic kidney disease in a patient, comprising administering to a patient in need of such treatment an effective amount of a compound of Formula I.

The present invention also provides a method of treating diabetic kidney disease in a patient, comprising administering to a patient in need of such treatment an effective amount of a compound of Formula I.

The present invention also provides a method of treating hypertension in a patient, comprising administering to a patient in need of such treatment an effective amount of a compound of Formula I.

In addition, the invention provides a compound of Formula I for use in therapy. The invention further provides a compound of Formula I for use in for the treatment of chronic kidney disease. In addition, the invention provides a compound of Formula I for use in the treatment of diabetic kidney disease. In addition, the invention provides a compound of Formula I for use in the treatment of hypertension. Furthermore, the invention provides the use of a compound of Formula I for the manufacture of a medicament for the treatment of chronic kidney disease. Furthermore, the invention provides the use of a compound of Formula I for the manufacture of a medicament for the treatment of diabetic kidney disease. The invention further provides the use of a compound of Formula I for the manufacture of a medicament for the treatment of hypertension.

The invention further provides a pharmaceutical composition, comprising a compound of Formula I with one or more pharmaceutically acceptable carriers, diluents, or excipients. The invention further provides a process for preparing a pharmaceutical composition, comprising admixing a compound of Formula I with one or more pharmaceutically acceptable carriers, diluents, or excipients. This invention also encompasses novel intermediates and processes for the synthesis of the compound of Formula I.

As used herein, the terms "treating", "treatment", or "to treat" includes prohibiting, restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art using known techniques and by observing results obtained under analogous circumstances. In determining the effective amount for a patient, a number of factors are considered by one skilled in the art, including, but not limited to: the patient's size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I is generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy, L. V. Allen, Editor, 22$^{nd}$ Edition, Pharmaceutical Press, 2012).

A pharmaceutically acceptable salt of the compound of the invention may be formed, for example, by reaction of an appropriate free base of the compound of the invention and an appropriate pharmaceutically acceptable acid in a suitable solvent under standard conditions well known in the art. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," Organic Process Research and Development, 4: 427-435 (2000); and Berge, S. M., et al., "Pharmaceutical Salts," Journal of Pharmaceutical Sciences, 66: 1-19, (1977).

Certain abbreviations are defined as follows: "ACN" refers to acetonitrile; "AcOH" refers to glacial acetic acid; "DBU" refers to 1,8-diazabicyclo[5.4.0]undec-7-ene; "DCM" refers to dichloromethane or methylene chloride; "DIPEA" refers to N,N-diisopropylethylamine; "DMF" refers to N,N-dimethylformamide; "DMSO" refers to dimethylsulfoxide; "EDCI" refers to 1-ethyl-3-(3-dimethylaminopropyl)carbodiimide; "ES/MS" refers to Electrospray Mass Spectrometry; "EtOAc" refers to ethyl acetate; "Et$_2$O" refers to diethyl ether; "EtOH" refers to ethanol; "HMDS" refers to hezamethyldisilazane; "HOBT" refers to hydroxybenzotriazole; "hr" refers to hour or hours; "IC$_{50}$" refers to the concentration of an agent that produces 50% of the maximal inhibitory response possible for that agent; "μmol" refers to micromole or micromoles; "min" refers to minute or minutes; "MeOH" refers to methanol or methyl alcohol; "MTBE" refers to methyl-tert-butyl ether; "NiNTA" refers to chromatography with an agarose stationary phase functionalized with nitrilotriacetic acid as chelator; "POCl$_3$" refers to phosphorus oxychloride; "RT" refers to room temperature; "SNAr" refers to nucleophilic aromatic substitution; "TEA" refers to triethylamine; "THF" refers to tetrahydrofuran; "Tris" refers to 2-Amino-2-hydroxymethyl-propane-1,3-diol; "U/ml" refers to units per milliliter; "wt" refers to weight.

The compounds of the present invention may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

Scheme 1

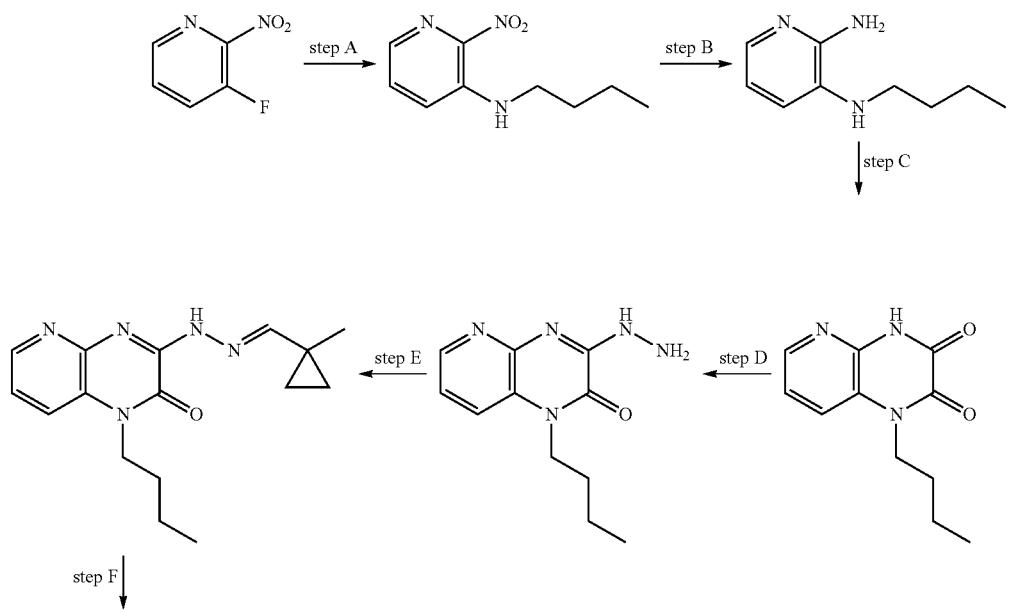

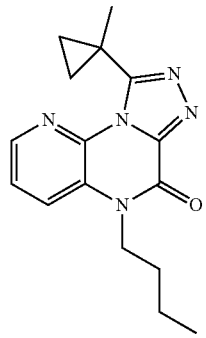

Formula I

Scheme 1 depicts the synthesis of the compound of Formula I. In Scheme 1, step A, SNAr reaction of 3-fluoro-2-nitropyridine, accomplished with various nucleophiles, is well appreciated in the art. For example, about 1 equivalent of 3-fluoro-2-nitropyridine is reacted with about 3 equivalents of butan-1-amine in a suitable polar solvent such as EtOH. The product can then be isolated utilizing techniques well known in the art, such as extraction. For example, the reaction mixture can be diluted with water and extracted with an appropriate polar organic solvent such as EtOAc. The organic extracts can be combined, dried over anhydrous sodium sulfate, filtered, and concentrated under reduced pressure to provide N-butyl-2-nitro-pyridin-3-amine, the product of step A, of sufficient purity for use in the next step without additional purification.

Subsequent reduction of the nitro group is well known in the art. In Scheme 1, step B, for example, about 1 equivalent of N-butyl-2-nitro-pyridin-3-amine, the product of step A, can be hydrogenated in the presence of an appropriate transition metal catalyst, such as palladium on carbon, in a variety of organic solvents, such as MeOH. The reduced product can then be isolated utilizing techniques well known in the art, such as filtration and evaporation. For example, the crude reaction mixture can be filtered through a bed of diatomaceous earth, and the filtrate can be concentrated under reduced pressure to obtain N3-butylpyridine-2,3-diamine, the product of Scheme 1, step B, of sufficient purity for use in the next step without additional purification.

Cyclization to the dione product of Scheme 1, step C, can be accomplished under thermal acylation conditions with diethyl oxalate in an appropriate organic solvent such as EtOH. For example, about 1 equivalent of N3-butylpyridine-2,3-diamine can be treated with about 5 equivalents of diethyl oxalate in a suitable polar organic solvent such as EtOH in a sealed tube at about 100° C. The cyclized product can then be isolated utilizing techniques well known in the art, such as precipitation and filtration. For example, the reaction mixture may be cooled to about −10 to 0° C., and the subsequent precipitate can be collected by filtration and washing with diethyl ether to obtain 1-butyl-4H-pyrido[2,3-b]pyrazine-2,3-dione, the product of Scheme 1, step C, of sufficient purity for use in the next step without additional purification.

Dehydration of an activated carbonyl with a nucleophile such as hydrazine is well appreciated in the art. For example, about 1 equivalent of 1-butyl-4H-pyrido[2,3-b]pyrazine-2,3-dione, the product of Scheme 1, step C, can be treated with about 5 equivalents of hydrazine monohydrate at about 100° C. in a pressurized tube. The product can then be isolated utilizing techniques well known in the art, such as precipitation and filtration. For example, the crude reaction mixture can be cooled to about 0° C., and the resulting precipitate can be collected by filtration and washing with diethyl ether to obtain 1-butyl-3-hydrazino-pyrido[2,3-b]pyrazin-2-one, the product of Scheme 1, step D, of sufficient purity for use in the next step without additional purification.

Subsequent alkylation of the hydrazine product of step D can be accomplished under various reductive amination techniques well known in the art. For example, about 1 equivalent of 1-butyl-3-hydrazino-pyrido[2,3-b]pyrazin-2-one, the product of Scheme 1, step D, may be treated with about 2 equivalents an appropriately substituted alkyl aldehyde, such as 1-methylcyclopropanecarbaldehyde (CAS #4515-89-3, Enamine LLC, USA), in an appropriate alcoholic solvent such as MeOH containing a catalytic amount of an appropriate acid, such as AcOH, at about RT to reflux. The product can then be isolated utilizing techniques well known in the art, such as crystallization and filtration. For example, the crude reaction mixture can be concentrated under reduced pressure, and the product can be obtained by crystallization with a suitable organic solvent such as hexanes, with subsequent filtration to collect 1-butyl-3-[2-[(1-methylcyclopropyl)methylene]hydrazino]pyrido[2,3-b]pyrazin-2-one, the product of Scheme 1, step E.

Preparation of the compound of Formula 1 can be achieved using a hypervalent iodine-mediated oxidative cyclization (R. Aggarwal & G. Sumran, *Synthetic Communications*, 36: 1873-1876, 2006) on the substituted imine 1-butyl-3-[2-[(1-methylcyclopropyl)methylene]hydrazino]pyrido[2,3-b]pyrazin-2-one in a suitable organic solvent, such as DCM, at temperatures ranging from 0° C. to RT. For example, about 1 equivalent of 1-butyl-3-[2-[(1-methylcyclopropyl)methylene]hydrazino]pyrido[2,3-b]pyrazin-2-one, the product of Scheme 1, step E, can be dissolved in DCM and treated with about 2 equivalents iodosobenzene diacetate (CAS #3240-34-4) at about 0° C. to RT. The product can then be isolated utilizing techniques well known in the art, such as extraction and chromatography. For example, the reaction mixture can be diluted with water and extracted with DCM. The layers can be separated and the organic layer is washed sequentially with saturated aqueous NaHCO₃, dried over Na₂SO₄, filtered, and concentrated under reduced pressure. The resulting residue can be purified by chromatography over silica, using a gradient of an appropriate solvent mixture such as EtOAc and hexanes, to give the compound of Formula I, the product of Scheme 1, step F.

Scheme 2

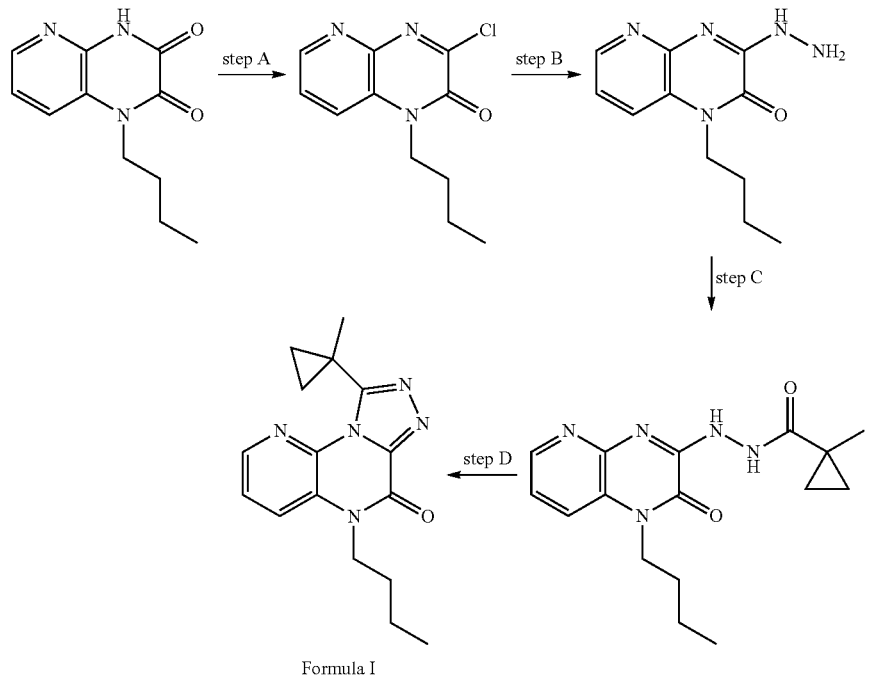

Formula I

Scheme 2 depicts an alternative synthesis of the compound of Formula I. In Scheme 2, step A, 1-butyl-4H-pyrido[2,3-b]pyrazine-2,3-dione, the product of Scheme 1, step C, can be converted to the chloro compound, as well known in the art, using a suitable chlorinating agent, such as POCl$_3$, SOCl$_2$, oxalyl chloride, or PCl$_5$, in an appropriate organic solvent such as DCM or ACN containing a catalytic amount of DMF at temperatures ranging from RT to reflux. For example, about 1 equivalent of 1-butyl-4H-pyrido[2,3-b]pyrazine-2,3-dione, the product of Scheme 1, step C, can be dissolved in ACN containing DMF, and the resulting reaction mixture can be treated with about 3 equivalents of thionyl chloride and heated to reflux for about 3 hr. The reaction mixture is concentrated under reduced pressure after cooling to ambient temperature to provide the product of Scheme 2, step A, 1-butyl-3-chloro-pyrido[2,3-b]pyrazin-2-one, suitable for subsequent use without further purification.

In Scheme 2, step B, chloride displacement can be achieved by treating about 1 equivalent of 1-butyl-3-chloro-pyrido[2,3-b]pyrazin-2-one, the product of Scheme 2, step A, with a solution of about 4 equivalents aqueous hydrazine monohydrate in a polar aprotic solvent such as THF at RT for about 8-24 hr. The product can then be isolated utilizing techniques well known in the art, such as extraction and azeotropic distillation. For example, the reaction mixture can be diluted with water and filtered, and the filter cake can be washed with a high-boiling suitable organic solvent such as toluene or MTBE, and the resulting water can be removed from the biphasic mixture by simple azeotropic distillation on a rotary evaporator under reduced pressure with a suitable high-boiling solvent, such as 2-methyl-tetrahydrofuran, to give 1-butyl-3-hydrazino-pyrido[2,3-b]pyrazin-2-one, the product of Scheme 2, step B.

Acylation of the product of step B can be accomplished with a suitable carboxylic acid using a variety of amide coupling techniques well known in the art. For example, about 1 equivalent of 1-butyl-3-hydrazino-pyrido[2,3-b]pyrazin-2-one, the product of Scheme 2, step B, can be coupled with about 1.5 equivalents of 1-methylcyclopropanecarboxylic acid in a suitable organic solvent, such as THF, DMF, or DMSO, containing about 1.5 equivalents of EDCI and 1.5 equivalents HOBT with subsequent addition of about 3-5 equivalents of a non-nucleophilic organic base such as DIPEA or TEA. The product can then be isolated utilizing techniques well known in the art, such as extraction. For example, the reaction mixture can be neutralized with a suitable mineral acid such as aqueous HCl diluted with water, and washed with a suitable organic solvent such as DCM, EtOAc, MTBE, or Et$_2$O. The layers can be separated, and the resulting aqueous layer can be basified to pH ~7-8 with an appropriate alkaline solid, such as K$_2$CO$_3$, NaHCO$_3$, or Na$_2$SO$_3$, with subsequent extraction with a suitable organic solvent such as DCM, EtOAc, or Et$_2$O. The organic layers can be sequentially washed with water, saturated aqueous NaCl, dried over Na$_2$SO$_4$, filtered, and the filtrate concentrated under reduced pressure to give N'-(1-butyl-2-oxo-pyrido[2,3-b]pyrazin-3-yl)-1-methyl-cyclopropanecarbohydrazide, the product of Scheme 2, step C.

In Scheme 2, step D, the compound of Formula 1 can be achieved by cyclization under thermal or microwave conditions well known in the art. For example, about 1 equivalent N'-(1-butyl-2-oxo-pyrido[2,3-b]pyrazin-3-yl)-1-methyl-cyclopropanecarbohydrazide can be heated for about 2-12 hr under reflux in a suitable solvent such as hexamethyldisilazane containing about 0.2 equivalents of a suitable non-nucleophilic organic base such as 1,8-diazabicyclo[5.4.0]undec-7-ene. The product can then be isolated utilizing techniques well known in the art, such as dilution, filtration, trituration, and chromatography. For example, the reaction mixture can be poured into water and the resulting precipitate can be collected by filtration, with subsequent partitioning of the collected solid between a suitable non-miscible mixture of an organic solvent, such as DCM, and water. The organic layer can be separated, washed sequentially with water and saturated aqueous NaCl, dried over $Na_2SO_4$, filtered, and concentrated under reduced pressure. The resulting residue can be triturated with a suitable hot or boiling organic solvent, such as EtOAc, for about 1 hr, and the resulting solid can be collected by filtration upon cooling. The solid may be further purified by chromatography over silica, using a gradient of an appropriate solvent mixture such as EtOAc and DCM, to give the compound of Formula I, product of Scheme 2, step D.

Preparation 1

N-butyl-2-nitro-pyridin-3-amine

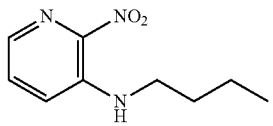

Scheme 1, step A: Dissolve 3-fluoro-2-nitropyridine (5.0 g, 35.2 mmol) in EtOH (30 mL) and cool the mixture to 0° C. in an ice bath. Add butan-1-amine (7.7 g, 105.6 mmol) to the mixture, allow the mixture to warm to RT, and stir at RT for 2 hr. Dilute the mixture with water and extract with EtOAc. Wash the organic layer with saturated aqueous NaCl, dry over $Na_2SO_4$, filter, and concentrate under reduced pressure to give the title compound (6.2 g, 90% yield) as yellow oil, suitable for use without additional purification. ES/MS m/z 196.1 (M+1).

Alternative Procedure for Preparation 1

Add 3-fluoro-2-nitropyridine (92 g, 0.65 mol) in EtOH (552 mL) at ~20-25° C. Cool the mixture to 0° C. in an ice bath. Add butan-1-amine (118.4 g, 1.6187 mol) at ~0-5° C. drop wise over 40 min Warm to ~20-25° C. and stir for 16 hr. Add water (800 mL) to the reaction mixture, extract with EtOAc (2×600 mL), separate the layers, and wash the combined organic layers with water (2×1 L), saturated aqueous NaCl (2×500 mL), dry over $Na_2SO_4$, filter, and concentrate under reduced pressure at 35° C. to obtain the title compound (120.00 g, 95% yield) as a deep yellow oil, suitable for use without additional purification. ES/MS m/z 196.1 (M+1).

Preparation 2

N3-butylpyridine-2,3-diamine

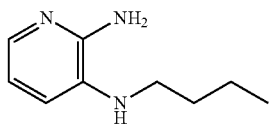

Scheme 1, step B: Add 5% Pd/C (3.0 g, 1.4 mmol) to a solution of N-butyl-2-nitro-pyridin-3-amine (6.0 g, 30.7 mmol) dissolved in MeOH (50 mL) under N2. Stir the mixture at RT under a balloon of $H_2$ for 8 hr. Filter the mixture through a pad of diatomaceous earth, wash with MeOH, and concentrate the filtrate under reduced pressure to give the title compound (5.0 g, 98% yield) as a black solid, suitable for use without additional purification. ES/MS m/z 166.1 (M+1).

Alternative Procedure for Preparation 2

Add N-butyl-2-nitro-pyridin-3-amine (128.0 g, 0.7 mol) in MeOH (1024 mL) at ~20-25° C. Add 5% wet Pd/C (64 g, 50% loading) at ~20-25° C. Stir the resulting mixture under 3 atm $H_2$ at ~20-25° C. for 3 hr. Filter the reaction mixture through diatomaceous earth, wash the filter cake with MeOH (5×500 mL), and concentrate the filtrate under reduced pressure to give the title compound (101.9 g, 94% yield) as a black solid, suitable for use without additional purification. ES/MS m/z 166.1 (M+1).

Preparation 3

1-butyl-4H-pyrido[2,3-b]pyrazine-2,3-dione

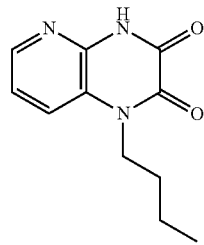 [SMILES: CCCCn1c(=O)c(=O)[nH]c2ncccc21]

Scheme 1, step C: Add diethyl oxalate (20.1 mL, 148.3 mmol) to a mixture of N3-butylpyridine-2,3-diamine (4.9 g, 29.65 mmol) in EtOH (30 mL). Heat the mixture in a sealed tube at 100° C. for 14 hr. Cool the reaction mixture to 0° C. and isolate the resulting solid by filtration. Wash the solid with $Et_2O$ and dry under vacuum at 40° C. to obtain the title compound (3.3 g, 51% yield) as a green colored solid, suitable for use without additional purification. ES/MS m/z 219.8 (M+1).

Alternative Procedure for Preparation 3

Add N3-butylpyridine-2,3-diamine (81.4 g, 0.5 mol) in EtOH (550 mL) at ~20-25° C. Add 30 wt % NaOEt in EtOH (427.4 g, 1.0 mol) in one portion at ~20-25° C. Add diethyl oxalate (87.1 g, 0.6 mol) drop wise at ~20-30° C. and stir at RT for 2.5 hr. Pour the reaction mixture into a mixture of 0.5 M aqueous HCl/DCM (1600 mL/1200 mL) at ~0-10° C. with stirring. Separate two layers, extract the aqueous layer with DCM (2×800 mL), wash with water (2×1600 mL), saturated aqueous NaCl (1600 mL), and dry over $Na_2SO_4$. Filter and concentrate the filtrate under reduced pressure. Slurry the resulting solid residue in ACN (200 mL) at ~20-25° C. for 30 min and isolate the resulting solid by filtration to give the title compound (70.0 g, 65% yield) as a green solid, suitable for use without additional purification. ES/MS m/z 220.1 (M+1).

Preparation 4

1-butyl-3-hydrazino-pyrido[2,3-b]pyrazin-2-one

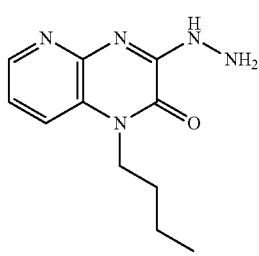 [SMILES: CCCCn1c(=O)c(NN)nc2ncccc21]

Scheme 1, step D: Add hydrazine monohydrate (3.55 mL, 73.0 mmol) to a mixture of 1-butyl-4H-pyrido[2,3-b]pyrazine-2,3-dione (3.2 g, 14.6 mmol) in EtOH (20 mL). Heat the mixture in a sealed tube at 100° C. for 14 hr. Cool the reaction mixture to 0° C. and isolate the solid by filtration. Wash the solid with Et$_2$O and dry under vacuum at 45° C. to obtain the title compound (2.8 g, 82% yield) as a green colored solid, suitable for use without additional purification. ES/MS m/z 234.2 (M+1).

Preparation 5

1-butyl-3-[2-[(1-methylcyclopropyl)methylene]hydrazino]pyrido[2,3-b]pyrazin-2-one

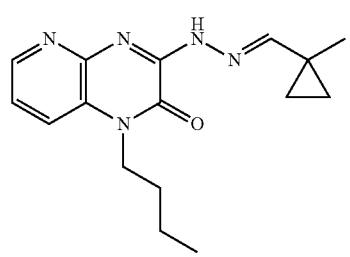 [SMILES: CCCCn1c(=O)c(N/N=C/C2(C)CC2)nc2ncccc21]

Scheme 1, step E: Add 1-methylcyclopropanecarbaldehyde (1.15 mL, 13.7 mmol) and AcOH (39.3 µL) to a mixture of 1-butyl-3-hydrazino-pyrido[2,3-b]pyrazine-2-one (1.6 g, 6.9 mmol) in MeOH (20 mL). Stir the mixture at RT for 1 hr. Concentrate the mixture under reduced pressure and recrystallize the product from hexane (50 mL). Isolate the solid by filtration and wash with hexane to obtain the title compound (1.30 g, 63% yield) as a black solid, suitable for use without additional purification. ES/MS m/z 300.2 (M+1).

Preparation 6

1-butyl-3-chloro-pyrido[2,3-b]pyrazin-2-one

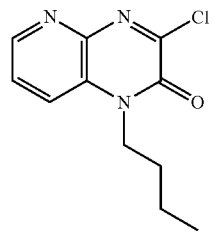 [SMILES: CCCCn1c(=O)c(Cl)nc2ncccc21]

Scheme 2, step A: Dissolve 1-butyl-4H-pyrido[2,3-b]pyrazine-2,3-dione (60.8 g, 0.3 mol) in ACN (10 mL/g, 600 mL) at ~20-25° C. Add DMF (4.2 mL) and add SOCl$_2$ (99.0 g, 0.8 mol) in one portion. Heat the resulting mixture to reflux at ~75-80° C. for 2.5 hr. Concentrate the reaction mixture to dryness under reduced pressure to give the crude title compound (93.0 g, >99% yield) as a black solid, suitable for use without additional purification. ES/MS m/z 238.1 (M+1).

Preparation 7

1-butyl-3-hydrazino-pyrido[2,3-b]pyrazin-2-one

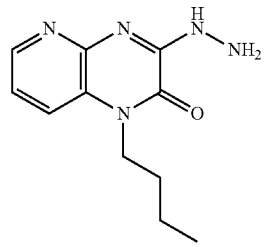 [SMILES: CCCCn1c(=O)c(NN)nc2ncccc21]

Scheme 2, step B: Add THF (900 mL) to an 85% (wt/wt %) aqueous solution of hydrazine monohydrate (48 g, 1.5 mol) at RT. Add 1-butyl-3-chloro-pyrido[2,3-b]pyrazin-2-one (90.0 g, 0.4 mol) to form a slurry and stir at RT for 16 hr. Add water (100 mL) to the reaction mixture and stir for 20 min. Filter and wash the filter cake with water (2×400 mL) followed by MTBE (2×400 mL). Remove water by azeotroping with 2-methyl-THF (3×600 mL) under reduced pressure to give the title compound (50.0 g, 75% yield) as a green solid, suitable for use without additional purification. ES/MS m/z 234.1 (M+1).

Preparation 8

N'-(1-butyl-2-oxo-pyrido[2,3-b]pyrazin-3-yl)-1-methyl-cyclopropanecarbohydrazide

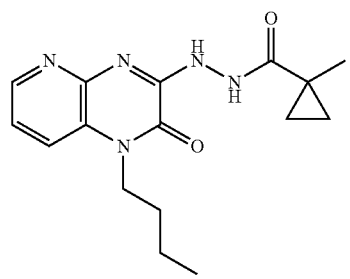 [SMILES: CCCCn1c(=O)c(NNC(=O)C2(C)CC2)nc2ncccc21]

Scheme 2, step C: Add 1-methylcyclopropanecarboxylic acid (30.9 g, 0.3 mol) to DMF (350 mL) at RT and cool the mixture to 0° C. At ~-5-0° C., add EDCI (61.0 g, 0.3 mol) followed by HOBT (41.75 g, 0.3 mol). At ~-10-0° C., add TEA (62.47 g, 0.6 mol) drop wise over 40 min and stir the resulting mixture at ~-5-0° C. for 20 min. Add 1-butyl-3-hydrazino-pyrido[2,3-b]pyrazin-2-one (48.0 g, 0.2 mol) at ~0-5° C. in one portion, warm to RT, and stir the resulting slurry for 16 hr. Pour the reaction mixture into 0.6 M aqueous HCl (1600 mL) and wash with MTBE (3×500 mL); separate the layers, discard the MTBE layer, and add DCM (1000 mL) to the aqueous layer. Adjust to pH ~7-8 with solid NaHCO$_3$ (140 g), separate the layers, extract the aqueous layer with DCM (3×600 mL), and wash the combined organic layers sequentially with water (3×1000 mL) and saturated aqueous NaCl (2×1000 mL). Evaporate under reduced pressure to give the title compound (45.0 g, 69% yield) as a black solid, suitable for use without additional purification. ES/MS m/z 316.2 (M+1).

EXAMPLE 1

5-butyl-9-(1-methylcyclopropyl)pyrido[3,2-e][1,2,4]triazolo[4,3-a]pyrazin-6(5H)-one

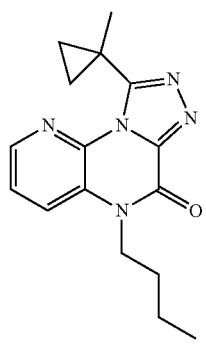 [SMILES: CCCCn1c(=O)c2nnc(C3(C)CC3)n2c2ncccc21]

Scheme 1, step F: Add 1-butyl-3-[2-[(1-methylcyclopropyl)methylene]-hydrazino]pyrido[2,3-b]pyrazin-2-one (1.3 g, 4.3 mmol) to DCM (15 mL) and cool the solution to 0° C. in an ice bath. Add iodosobenzene diacetate (2.9 g, 8.7 mmol) to the solution and stir the mixture at RT for 1 hr. Quench the reaction mixture with water and extract with DCM. Wash the organic layers with saturated NaHCO$_3$, dry over Na$_2$SO$_4$, filter, and concentrate under reduced pressure, and purify the resulting residue by chromatography over silica, eluting with EtOAc:hexanes (3:1), to obtain the title compound (1.1 g, 85% yield) as an off-white solid. ES/MS m/z 298.2 (M+1).

Alternative Procedure for Example 1

Scheme 2, step D: Slurry N'-(1-butyl-2-oxo-pyrido[2,3-b]pyrazin-3-yl)-1-methyl-cyclopropanecarbohydrazide (45.0 g, 0.1 mol) in HMDS (360 mL) at RT. Add DBU (4.34 g, 28.5 mmol) and heat to 125° C. Stir the resulting solution for 6 hr under reflux. Cool the reaction mixture to RT, pour the mixture into water (800 mL), and filter and collect the resulting solid. Dissolve the solid in DCM (400 mL)/H$_2$O (100 mL), separate the resulting layers, and wash the organic phase with saturated aqueous NaCl (100 mL), dry over Na$_2$SO$_4$, filter, and concentrate the filtrate under reduced pressure to give a residue. Triturate with EtOAc (200 mL) at 40-50° C. for 1 h, and isolate the resulting solid (22.0 g, 98% purity as determined by LCMS) by filtration. Combine the 22.0 g batch with another batch of material (10.0 g, 100% purity as determined by LCMS) and further purify by chromatography over silica gel, eluting with DCM:EtOAc (1:1), to obtain a residue after solvent evaporation. Triturate the resulting residue with hot EtOAc for 30 min and isolate the resulting solid by filtration to give the title compound (25.70 g, 42% yield) as a white solid. ES/MS m/z 298.2 (M+1).

Generation of PDE Proteins

The nucleotide sequences encoding full-length human PDE1A (NP_001003683.1), PDE1C (NP_005011.1), PDE5A (NP_001074.2), PDE7B (NP_061818.1) and PDE9A (NP_002597.1) are inserted into pFastBac1 (Invitrogen) vector with an N-terminal HIS tag. The nucleotide sequences encoding full-length human PDE4D (NP_006194.2) and catalytic domain (residue 641-1141) of PDE3A (NP_000912.3) are inserted into pFastBac1 (Invitrogen) vector with a C-terminal HIS tag. The nucleotide sequences encoding full-length human PDE8A (NP_002596.1) and PDE11A (AAI12394.1) are inserted into pFastBac1 (Invitrogen) vector with an N-terminal Flag tag. The nucleotide sequences encoding full-length human PDE10A (AAD32595.1) are inserted into pFastBac1 (Invitrogen) vector with a C-terminal Flag-His tag. The nucleotide sequences encoding full-length human PDE6A (NP_000431.2) and PDE6B (AAH00249.1) are inserted into pFastBacDual (Invitrogen) vector with an N-terminal HIS tag and N-terminal Flag tag, respectively, for production of PDE6A/6B dimer. Baculovirus generation and protein expression in Sf9 cells are carried out according to the protocol of Bac-to-Bac Baculovirus Expression system (Invitrogen). The nucleotide sequences encoding full-length human PDE1B (NP_000915.1) and PDE2A (NP_002590.1) are inserted into pIEX4 (Novagen) with a C-terminal HIS tag, and both protein productions in Sf9 cells are carried out according to the vendor's protocol (Novagen). The His tagged PDE proteins are purified using Ni-NTA agarose (Qiagen) followed by size exclusion chromatography on a SUPERDEX® 200 column (GE Healthcare) in storage buffer (20 mM Tris-HCl, pH7.5, 150 mM NaCl, 10% Glycerol). The Flag tagged PDE proteins including PDE6A/6B are purified using anti-Flag M2-agarose (Sigma), after purification through NiNTA column chromatography and eluted in storage buffer (50 mM Tris-HCl, pH7.5, 150 mM NaCl, 10% Glycerol, 0.1 mg/ml Flag peptide). All purified proteins are stored at −80° C. in small aliquots.

Phosphodiesterase Enzyme Assays

All 3′, 5′ cyclic nucleotide phosphodiesterase (PDE) enzyme activities are measured with a radiometric enzyme assay based on SPA detection system (scintillation proximity assay). Compounds to be tested are diluted in pure dimethyl sulfoxide (DMSO) using ten point concentration response curves. Maximal compound concentration in the reaction mixture is either 10 or 100 µM. Compounds at the appropriate concentration are pre-incubated with either of the PDE enzymes for 30 minutes before the reaction is started by the addition of substrate. Reactions are allowed to proceed for 60 minutes at room temperature. Next, reactions are stopped by addition of SPA beads. Samples are read 12 hours later in a MICROBETA™ TRILUX® Counter. "$IC_{50}$" refers to the concentration of the compound that produces 50% of the maximal inhibitory response possible for that compound. $IC_{50}$ values are calculated by plotting the normalized data vs. log [compound] and fitting the data using a four parameter logistic equation.

$Ca^{2+}$-Calmodulin Dependent PDE Enzyme Assays

PDE1B, PDE1A, and PDE1C are cloned and purified following standard protein generation procedures. The assay buffer is prepared to give a final concentration in the assay of 50 mM Tris-HCl, 50 mM $MgCl_2$, 4 mM $CaCl_2$, 0.1% Bovine serum albumin and 6 U/ml Calmodulin in water, at pH 7.5. The final enzyme concentration is 0.25, 0.074 and 0.0012 nM, for PDE1A, PDE1B and PDE1C respectively. The reactions are started by addition of the substrate, [$^3$H] cAMP, to give a final concentration of 47 nM.

TABLE 1

In vitro potency of Example 1 against human PDE1A, PDE1B, and PDE1C.

| PDE enzymes | $IC_{50}$ (nM) of Example 1 |
| --- | --- |
| PDE 1A | 10.9 ± 2.6 |
| PDE 1B | 16.3 ± 9.1 |
| PDE 1C | 2.65 ± 0.9 |

The data in Table 1 demonstrate that the compound of Example 1 inhibits human PDE1A, PDE1B, and PDE1C enzyme activity in vitro.

PDE Enzyme Assays Using [$^3$H]cAMP as Substrate

The following phosphodiesterase activities are measured using [$^3$H]cAMP as reaction substrate: human PDE3A (catalytic domain), human PDE4D, human PDE7B and human PDE8A. All these enzymes are cloned and purified following standard procedures. The assay buffer is prepared to give a final concentration in the assay of 50 mM Tris-HCl, 8.3 mM $MgCl_2$, 1.7 mM ethylenediaminetetraacetic acid (EDTA) and 0.1% Bovine serum albumin at pH 7.5. Final enzyme concentrations are 0.008, 0.021, 0.5 and 0.06 nM for PDE3A, PDE4D, PDE7B and PDE8A respectively. Reactions are started by addition of the substrate, [$^3$H]cAMP, to give a final concentration of 47 nM.

TABLE 2

In vitro potency of Example 1 against human PDE3A (catalytic domain), PDE4D, PDE7B and PDE8A.

| PDE enzymes | $IC_{50}$ (nM) of Example 1 |
| --- | --- |
| PDE3A | >100000 |
| PDE4D | 11900 ± 1580 |
| PDE7B | 4170 |
| PDE8A | >10000 |

PDE Enzyme Assays Using [$^3$H]cGMP as Substrate

The following phosphodiesterase activities are measured using [$^3$H]cGMP as reaction substrate: human PDE2A, human PDE5A, human PDE6A/6B, human PDE9A, human PDE10A and human PDE11A. The catalytic active form of human PDE6 is a dimer composed of a α (human PDE5A) and β subunits (human PDE6B). The dimer of human PDE6A/6B is produced by the expression and purification strategy, using two purification steps, i.e., NiNTA and anti-FLAG Sepharose chromatography. The rest of the enzymes are cloned and purified in house following standard procedures. The assay buffer is prepared to give a final concentration in the assay of 50 mM Tris-HCl, 8.3 mM $MgCl_2$, 1.7 mM EDTA and 0.1% Bovine serum albumin at pH 7.5. Final enzyme concentrations are 0.2, 0.002, 5, 1, 0.03 and 0.03 nM for human PDE2A, human PDE5A, human PDE6AB, human PDE9A, human PDE10A and human PDE11A, respectively. The reactions are started by addition of the substrate, [$^3$H]cGMP, to give a final concentration of 80 nM in the case of human PDE2A, human PDE10A, human PDE5A, human PDE6AB and human PDE11A assays, whereas for human PDE9A 20 nM of [$^3$H]cGMP is used.

TABLE 3

In vitro potency of Example 1 against PDE2A, PDE5A, PDE6AB, PDE9A, PDE10A and PDE11A.

| PDE enzymes | $IC_{50}$ (nM) of Example 1 |
| --- | --- |
| PDE2A | >10000 |
| PDE5A | 3130 |
| PDE 6AB | 2460 ± 247 |
| PDE9A | >10000 |
| PDE10A | 9340 |
| PDE11A | 389 ± 179 |

The data in Tables 1, 2, and 3 demonstrate that the compound of Example 1 is a selective inhibitor of human PDE1A, PDE1B, and PDE1C relative to human PDE2A, PDE3A, PDE4D, PDE5A, PDE6AB, PDE7B, PDE8A, PDE9A, PDE10A, and PDE11A in vitro.

We claim:
1. A compound of the formula:

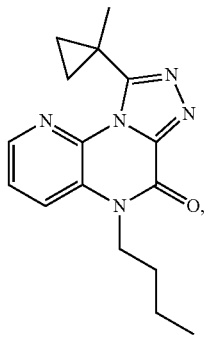 [SMILES: CCCCn1c(=O)c2nnc(C3(C)CC3)n2c2ncccc21]

or a pharmaceutically acceptable salt thereof.

2. The compound according to claim 1 which is:

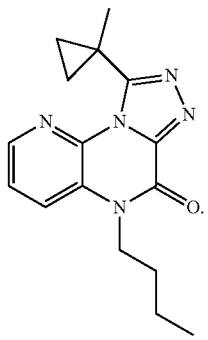 [SMILES: CCCCn1c(=O)c2nnc(C3(C)CC3)n2c2ncccc21]

3. A method of treating chronic kidney disease in a patient, comprising administering to a patient in need thereof an effective amount of a compound of claim 1, or a pharmaceutically-acceptable salt thereof.

4. A method of treating diabetic kidney disease in a patient, comprising administering to a patient in need thereof an effective amount of a compound of claim 1, or a pharmaceutically-acceptable salt thereof.

5. A pharmaceutical composition, comprising a compound or a pharmaceutically-acceptable salt thereof according to claim 1, with one or more pharmaceutically acceptable carriers, diluents, or excipients.

6. A process for preparing a pharmaceutical composition, comprising admixing a compound according to claim 1, or a pharmaceutically-acceptable salt thereof, with one or more pharmaceutically acceptable carriers, diluents, or excipients.

7. A method of treating chronic kidney disease in a patient, comprising administering to a patient in need thereof an effective amount of a compound of claim 2.

8. A method of treating diabetic kidney disease in a patient, comprising administering to a patient in need thereof an effective amount of a compound of claim 2.

9. A pharmaceutical composition, comprising a compound according to claim 2, with one or more pharmaceutically acceptable carriers, diluents, or excipients.

10. A process for preparing a pharmaceutical composition, comprising admixing a compound according to claim 2 with one or more pharmaceutically acceptable carriers, diluents, or excipients.

* * * * *